United States Patent [19]

Sikorski et al.

[11] 4,401,604
[45] Aug. 30, 1983

[54] PROCESS FOR PREPARING THIOSULFENAMIDE DERIVATIVES OF N-PHOSPHONOMETHYLGLYCINE TRIESTERS

[75] Inventors: James A. Sikorski, West Lafayette, Ind.; Mary A. Hoobler, Creve Coeur, Mo.

[73] Assignee: Monsanto Company, St. Louis, Mo.

[21] Appl. No.: 309,328

[22] Filed: Oct. 5, 1981

[51] Int. Cl.$^3$ .............................................. C07F 9/32
[52] U.S. Cl. .................................. 260/968; 548/221; 260/941
[58] Field of Search .......................... 568/26; 260/968; 548/221

[56] References Cited

U.S. PATENT DOCUMENTS

| | | | |
|---|---|---|---|
| 2,123,082 | 7/1938 | Schulze | 568/26 |
| 3,155,720 | 11/1964 | Aichenegg et al. | 568/26 |
| 4,120,689 | 10/1978 | Dutra | 71/86 |
| 4,201,733 | 5/1980 | Nelson | 260/968 |

*Primary Examiner*—Anton H. Sutto
*Attorney, Agent, or Firm*—Arnold H. Cole; Howard C. Stanley; Gordon F. Sieckmann

[57] ABSTRACT

This invention relates to a process for preparing sulfenyl chloride derivatives of N-phosphonomethylglycine triesters which are useful as herbicides or intermediates for the production of thiosulfenamide derivatives of N-phosphonomethylglycine triesters compounds which are useful as herbicides.

37 Claims, No Drawings

PROCESS FOR PREPARING THIOSULFENAMIDE DERIVATIVES OF N-PHOSPHONOMETHYLGLYCINE TRIESTERS

This invention relates to a process for preparing sulfenyl chloride derivatives of N-phosphonomethylglycine triesters which are useful as herbicides or intermediates for the production of thiosulfenamide derivatives of N-phosphonomethylglycine triesters compounds which are useful as herbicides.

U.S. Pat. No. 4,120,689, issued to Gerard A. Dutra on Oct. 17, 1978, discloses alkyl-[di(benzyl) or di(aryl)] esters of N-phosphonomethyl glycine prepared by the reaction of a dibenzyl or diaryl phosphite with an N-methylene lower alkyl glycinate trimer. These esters and the hydrolysis products thereof containing at least one benzyloxy or aryloxy group bonded to the phosphorus atom thereof are disclosed as compounds having the formula

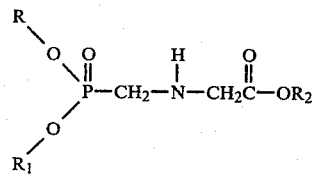

wherein R of U.S. Pat. No. 4,120,689, supra is disclosed as a member of the group consisting of phenyl, benzyl, naphthyl, biphenylyl, benzyloxyphenyl and phenyl, benzyl or naphthyl groups substituted with from 1 to 3 groups selected from the class consisting of hydroxyl, lower alkyl, lower alkoxy, lower alkylthio, trifluoromethyl, carbo (lower alkoxy), nitro, or halo; $R_1$ of U.S. Pat. No. 4,120,689, supra is hydrogen or an R group, and $R_2$ of U.S. Pat. No. 4,120,689, supra is a lower alkyl group or hydrogen and the strong acid salts of the compounds wherein neither $R_1$ or $R_2$ is H. A post-emergent herbicide utility is disclosed.

In accordance with the present invention, thiosulfenamide derivatives of N-phosphonomethylglycine of the formula

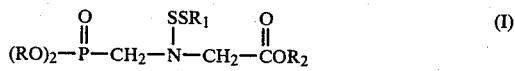

wherein R is selected from the group consisting of phenyl, naphthyl, biphenylyl; or phenyl, naphthyl or biphenylyl substituted with from 1 to 3 substituents independently selected from the group consisting of lower alkyl, lower alkoxy, lower alkylthio, lower alkoxycarbonyl, methylenedioxy, trifluoromethyl, cyano, nitro and halogen; and $R_1$ is independently alkyl, cycloalkyl, aralower alkyl, phenyl, naphthyl, or phenyl or naphthyl substituted with from 1 or 3 substituents selected from the group consisting of lower alkyl, lower alkoxy, halogen, trifluoromethyl and $R_2$ is lower alkyl or aralower alkyl are prepared by reacting a compound of the formula

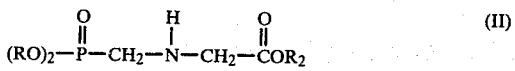

wherein R and $R_2$ are as aforedefined with sulfur dichloride in an aprotic solvent and in the presence of a hydrogen chloride acceptor to form a compound of the formula

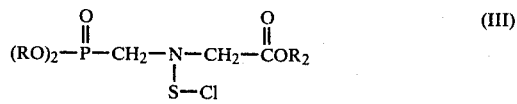

wherein R and $R_2$ are as aforedefined.

The reaction temperature for the aforerecited reaction is in the range from about $-50°$ to about $100°$ C., and is preferably from about $-30°$ C. to about $+10°$ C. although greater or lower temperatures may be employed if desired.

In preparing the compounds of formula (III), the ratio of reactants of formula (II) and and sulfur dichloride, is not narrowly critical. For best results, however, for each mole of a compound of formula (II), one should employ one mole of sulfur dichloride to produce one mole of a compond of formula (III). It is preferred to employ an excess of sulfur dichloride for ease of reaction and maximum yield of product of formula (III). A 2:1 adduct byproduct and an amine hydrochloride formed along with a compound of formula (III) are generally separated therefrom as a precipitate.

When practicing the process of this invention, it is preferred to add a compound of formula (II) to thee sulfur dichloride rather than vice versa so as to minimize the possibility of having excess comound of formula (II) in the presence of sulfur dichloride whereby a bis glyphosate adduct could be formed.

The compound of formula (III) is reacted with a thiol compound of the formula

wherein $R_1$ is as aforedefined, in the presence of a hydrogen chloride acceptor to form a compound of formula (I).

In reacting a compound of formula (III) with a compound of formula (IV), the temperature is in the range from about $-30°$ C. to about $100°$ C. and is preferably from about $-10°$ C. to about $+30°$ C. although greater or lower temperatures may be employed if desired.

The ratio of compounds of formula (III) and (IV) is not critical. For best results, however, one should employ for each mole of a compound of formula (III) a mole of a compound of formula (IV). Typically a molar excess of compound of formula (IV) is employed.

Typical compounds which may be employed as a compound of formula (IV) include thiol compounds such as methyl, ethyl, butyl, isopropyl, isopentyl, octyl, tertiary butyl, cyclohexyl, phenethyl, naphthyl, mercaptans, and thiophenols substituted with lower alkoxy, trifluoromethyl, lower alkyl, and halogen.

It is preferred that R is phenyl or phenyl substituted with lower alkoxy in the ortho or para position or substituted with halogen. $R_1$ is preferably alkyl such as methyl, isopropyl, octyl, phenethyl, or cyclohexyl, t-butyl, phenyl or phenyl substituted with lower alkyl, lower alkoxy or trifluoromethyl.

Illustrative of the substituted phenyl groups which R and $R_1$ independently represent are mono-substituted phenyl wherein the substituent is in the ortho, meta or para position, for example, methylphenyl, butylphenyl, methoxyphenyl, butoxyphenyl, fluorophenyl, chlorophenyl, bromophenyl, iodophenyl, trifluoromethyl-phenyl, nitrophenyl, methylthiophenyl, butylthiophenyl, cyanophenyl, ethoxycarbonylphenyl, and the like, and the di- and tri-substituted phenyl groups wherein the substituents are the same or different and are located in the 2, 3, 4, 5 or 6 positions of the phenyl ring, for example, dichlorophenyl, dimethylphenyl, methylchlorophenyl, ethylfluorophenyl, dibutoxyphenyl, butylnitrophenyl, methylthiochlorophenyl, di(ethylthio)phenyl, trimethylphenyl, trichlorophenyl, tributylphenyl, ethyldichlorophenyl and the like.

Groups representative of a substituted naphthyl group represented by R include methylnaphthyl, nitronaphthyl, bromonaphthyl, dimethylnaphthyl, difluoronaphthyl, trimethylnaphthyl and the like.

Groups representative of substituted biphenylyl groups represented by R include methylbiphenylyl, nitrobiphenylyl, bromobiphenylyl, dimethylbiphenylyl, difluorobiphenylyl, trimethylbiphenylyl and the like.

As employed herein, the term "lower alkyl" designates alkyl radicals which have from 1 to 4 carbon atoms in a straight or branched chain, for example, methyl, ethyl, propyl, isopropyl, butyl, isobutyl, sec-butyl, and t-butyl.

As employed herein, the term "alkyl" includes alkyl and substituted alkyl radicals having 1 to 8 carbon atoms therein, in a straight or branched chain therein.

The term "halo" or "halogen" as employed herein means chlorine, bromine, iodine and fluorine.

The term "lower alkoxy" includes groups representative of the term "lower alkyl" in combination with oxygen and includes methoxy, ethoxy, propoxy, butoxyy mixtures thereof and the like.

The term "lower alkylthio" includes representatives of lower alkyl in combination with sulfur.

The term "lower alkoxycarbonyl" includes groups representative of the aforedefined term "lower alkoxy" in combination with a carbonyl group.

As employed herein the term "aralower alkyl" includes combinations of those groups as aforedefined for the term "lower alkyl" with aryl groups such as phenyl, benzyl, naphthyl and biphenylyl.

The hydrogen chloride acceptor is typically an amine, preferably a tertiary amine, which will not react with the reactants employed or products formed. Examples of suitable tertiary amine hydrogen chloride acceptors include trimethylamine, triethylamine, tributylamine, trihexylamine, 1,5-diazabicyclo-[5.4.0]-undec-5-ene, pyridine, quinoline, mixtures thereof and the like.

Due to the reactive nature of the various reaction intermediates and reactants, the process of the present invention should be conducted in an aprotic solvent under essentially anhydrous conditions. Illustrative of the aprotic solvents employed in the process of this invention include benzene, toluene, dichloromethane, tetrahydrofuran, cyclohexane, methylcyclohexane, hexane, octane, dioxane, ethyl ether and the like, although a solvent is not required.

While the processes of this invention can be conducted at atmospheric, sub-atmospheric or super-atmospheric pressure, for convenience and economy it is generally preferred to conduct these processes at atmospheric pressure.

Those of skill in the art will recognize that preparation of the intermediate sulfenyl chloride is independent of the substitution on the R group. Preparation of intermediate sulfenyl chloride involving substitution on the R group is disclosed in applicants' patent application Ser. No. 309,324, "Aminosulfenamide Derivatives of N-Phosphonomethylglycinonitriles" simultaneously filed. Co-pending patent application Ser. No. 309,322, "Thiosulfenamide Derivatives of N-Phosphonomethylglycine Triesters" illustrates herbicidal activity of products prepared therefrom.

The following illustrative, non-limiting examples will serve to further demonstrate to those skilled in the art the manner in which specific compounds within the scope of this invention can be prepared. In the examples, all parts are parts by weight unless otherwise expressly stated.

General Procedure for the Preparation of Glyphosate Triester Thiolsulfenamides for Examples I, II, III, IV, and V hereafter following An oven-dried 1 liter flask was cooled under nitrogen, and charged with sulfur dichloride (0.05 mol) and 300 ml of toluene and cooled to $-20°$ C. To it was added a toluene solution of a triester of formula (II) (0.05 mol) corresponding to the particular thiosulfenamide desired at such a rate that the temperature did not exceed $-5°$ C. The yellow reaction mixture was stirred at $-20°$ C. for $3\frac{1}{2}$ hours. The supernatant liquid was removed under nitrogen and concentrated in vacuo to yield the desired intermediate compound of formula (III) as an oil. A toluene solution of the oil was added slowly to a solution of the appropriate mercaptan of formula (IV) in triethylamine in toluene at $5°$ C., maintaining the temperature below $10°$ C. The yellow reaction mixture was stirred for 3-4 hours, with slow warming to room temperature. The triethylamine hydrochloride was removed by filtration and the filtrate was washed with cold 10% aqueous sodium hydroxide, cold water, dried over $MgSO_4$, and concentrated in vacuo to an oil. Purification by HPLC gave the desired thio-sulfenamide product of the formula (I) as a yellow oil. $^1H$ NMR, $^{31}P$ NMR, and elemental analyses were all consistent with pure products.

EXAMPLE I

Glycine, N-[(diphenoxyphosphinyl)methyl]-N-[(1-methylethyl)dithio]-, methyl ester corresponding to a compound of formula (I) wherein R is phenyl, $R_1$ is isopropyl and $R_2$ is methyl was prepared as a yellow oil having a refractive index of 1.5567 at $22.3°$ C. and an analysis for $C_{19}H_{24}NO_5PS_2$: Calculated: C, 51.69; H, 5.48; N, 3.17; S, 14.52; Found: C, 51.67; H, 5.50; N, 3.15; S, 14.57.

EXAMPLE II

Glycine, N-[(diphenoxyphosphinyl)methyl]-N-(octyldithio)-, methyl ester corresponding to a compound of formula (I) wherein R is phenyl, $R_1$ is n-octyl, and $R_2$ is methyl was prepared as a yellow oil having a refractive index of 1.5415 at $22.3°$ C. and an analysis for $C_{24}H_{34}NO_5PS_2$: Calculated: C, 56.34; H, 6.70; N, 2.74; S, 12.53; Found: C, 56.37; H, 6.64; N, 2.63; S, 12.05.

EXAMPLE III

Glycine, N-(cyclohexyldithio)-N-[(diphenoxyphosphinyl)methyl]-, phenylmethyl ester corresponding to a compound of formula (I) wherein R is phenyl, $R_1$ is cyclohexyl, and $R_2$ is phenylmethyl was prepared as a yellow oil having a refractive index of 1.5752 at $25°$ C. and an analysis for $C_{28}H_{32}NO_5PS_2$: Calculated: C, 60.31; H, 5.78; N, 2.51; S, 11.50; Found: C, 59.96; H, 5.73; N, 2.34; S, 10.67.

EXAMPLE IV

Glycine, N-[(diphenoxyphosphinyl)methyl]-N-[(2-phenylethyl)dithio]-, phenylmethyl ester corresponding to a compound of formula (I) wherein R is phenyl, $R_1$ is phenylethyl, and $R_2$ is phenylmethyl was prepared as a yellow oil having a refractive index of 1.5956 at 23° C. and an analysis for $C_{30}H_{30}NO_5PS_2$: Calculated: C, 62.16; H, 5.22; N, 2.42; S, 11.06; Found: C, 60.90; H, 5.29; N, 2.23; S, 10.08.

EXAMPLE V

Glycine, N-[[Bis(2-methoxyphenoxy)phosphinyl]methyl]-N-[(3-trifluoromethyl)phenyl)dithio]-, methyl ester corresponding to a compound of formula (I) wherein R is 2-methoxyphenyl, $R_1$ is 3-trifluoromethylphenyl, and $R_2$ is methyl was prepared as a yellow oil having a refractive index of 1.5685 at 21.8° C. and an analysis for $C_{25}H_{25}F_3NO_7PS_2$: Calculated: C, 49.75; H, 4.17; N, 2.32; S, 10.62; Found: C, 49.60; H, 4.22; N, 2.27; S, 10.70.

EXAMPLE VI

Glycine, N-[[bis(4-methoxyphenoxy)phosphinyl]methyl]-N-(methyldithio)-, ethyl ester. An oven-dried 500 ml flask, cooled under nitrogen, was charged with 200 ml of toluene and cooled to −20° C. and the sulfur dichloride (8.7 g, 0.085 mol) was added. To this solution was added slowly via cannula a toluene solution of glyphosate triester, glycine, N-[(di(4-methoxyphenoxy)phosphinyl)methyl], -ethyl ester (34.8 g, 0.085 mol) at such a rate to maintain the temperature below −10° C. The green reaction mixture was stirred for 3½ hours at −20° C. The supernatant liquid was removed under nitrogen and concentrated in vacuo to 22 g (54% crude) of a dark oil. A toluene solution of the oil was added slowly via cannula to a solution of excess methyl mercaptan and two equivalents of triethylamine in toluene at 0° C. The rate of addition was such that the temperature did not exceed 10° C. The reaction mixture was stirred under nitrogen for 2 hours, allowing to slowly warm to room temperature. The triethylamine hydrochloride was removed by filtration and the filtrate was washed with cold 10% aqueous sodium hydroxide, cold water, dried over $MgSO_4$, filtered, and concentrated to an oil. Purification on a Waters Prep Pak 500 silica gel column, eluting with 40% ethylacetate/60% cyclohexane gave the desired product as a yellow oil, 3.4 g (30%) corresponding to a compound of formula (I) wherein R is 4-methoxyphenyl, $R_1$ is methyl, and $R_2$ is ethyl. $n_D^{22.4} = 1.5580$ having an analysis for $C_{20}H_{26}N_1O_7P_1S_2$: Calculated: C, 49.27; H, 5.38; N, 2.87; S, 13.15. Found: C, 49.35; H, 5.39; N, 2.81; S, 13.09.

EXAMPLE VII

An oven-dried 500 ml flask was charged with 200 ml of toluene, cooled to −20° C., and charged with sulfur dichloride (2.0 g, 0.02 mol). To this solution was added slowly via cannula a toluene solution of glycine, N-[[bis(4-chloro-3-methylphenoxy)phosphinyl]methyl]-, ethyl ester (7.0 g, 0.016 mol) and triethylamine, maintaining the temperature below −10° C. The reaction mixture was stirred at −20° C. for 2½ hours. The supernatant liquid was removed under nitrogen and slowly added via cannula to a solution of 4-methoxybenzenethiol (2.2 g, 0.016 mol) and triethylamine in toluene at −10° C. The reaction mixture was stirred overnight. The triethylamine hydrochloride was removed by filtration and the brown filtrate was washed with cold 10% aqueous sodiumhydroxide and cold water, dried over magnesium sulfate, filtered and concentrated in vacuo to 7.2 g of brown oil. Purification by HPLC on a Waters Prep Pak 500 silica gel column, eluting with 10% ethylacetate, 90% cyyclohexane yielded 1.3 g of yellow oil corresponding to a compound of formula (I) wherein R is 4-chloro-3-methylphenyl, $R_1$ is 4-methoxyphenyl and $R_2$ is ethyl. The product had a refractive index of 1.5738 at 24° C. and an elemental analysis for $C_{26}H_{28}Cl_2NO_6PS_2$: Calculated: C, 50.65; H, 4.58; N, 2.27; S, 10.40 Found: C, 50.39; H, 4.61; N, 2.23; S, 10.52.

EXAMPLE VIII

An oven-dried 500 ml flask cooled under nitrogen was charged with 150 ml of toluene, cooled to −20° C. and sulfur dichloride (6.2 g, 0.06 mol) was added. To this solution was added slowly via cannula a solution of glycine, N-[(diphenoxyphosphinyl)methyl]-, methyl ester (20.0 g, 0.06 mol) and excess triethylamine in 150 ml of toluene, at such a rate that the temperature did not exceed −10° C. The orange-yellow reaction mixture was stirred at −20° C. for 2½ hours. The supernatant liquid was removed under nitrogen and added slowly via cannula to a solution of tert-butyl mercaptan (5.4 g, 0.06 mol) and excess triethylamine in 100 ml of toluene at −20° C. The reaction mixture was allowed to slowly warm to room temperature and was stirred overnight. The triethylamine hydrochloride was removed by filtration and the filtrate was washed with cold 10% aqueous NaOH followed by cold water, dried over $MgSO_4$, filtered and concentrated in vacuo. Purification by HPLC on a Waters Prep Pak 500 silica gel column gave 11.5 g of clear oil, $n_D^{23.4} = 1.5535$, corresponding to a compound of formula (I) glycine, N-[(1,1-dimethylethyl)dithio]-N-[(diphenoxyphosphinyl)methyl]-, methyl ester wherein R is phenyl, $R_2$ is methyl and $R_1$ is tert-butyl and having analysis for $C_{20}H_{26}NO_5PS_2$: Calculated: C, 52.73; H, 5.75; N, 3.07; S, 14.08; Found: C, 52.68; H, 5.76; N, 3.06; S, 14.03.

Other compounds which it is believed may be prepared according to the aforedescribed process include: glycine, N-[[bis(4-methoxyphenoxy)phosphinyl]methyl]-N-[(1,1-dimethylethyl)dithio]-, ethyl ester; glycine, N-[(1,1-imethylethyl)dithio]-N-[(diphenoxyphosphinyl)methyl]-, phenylmethyl ester; glycine, N-[(diphenoxyphosphinyl)methyl]-N-[(4-methylphenyl)dithio]-, methyl ester; glycine, N-[[bis(4-methoxyphenoxy)phosphinyl]methyl)-N-(2-naphthalenyl)dithio]-, phenylmethyl ester; and glycine, N-[[bis(4-methoxyphenoxy)phosphinyl]-methyl]-N-[(4-chlorophenyl)dithio]-, phenylmethyl ester.

The preparation and herbicidal efficacy of these compounds is shown in copending patent application Ser. No. 309,322, "Thiosulfenamide Derivatives of N-Phosphonomethylglycine Triesters" filed simultaneously herewith.

The term "cycloalkyl" includes those cyclic arrangements of carbon and hydrogen atoms having 3 to 8 carbon atoms therein and includes cyclophntane, cyclopropane, cyclobutane, cyclohexane, cyclooctane and the like.

Typical groups representative of the term "aralower alkyl" include phenylmethyl, phenylethyl, phenylpropyl, phenylbutyl and the like.

EXAMPLE IX

The post-emergence herbicidal activity of some of the various compounds of this invention was demonstrated by greenhouse testing in the following manner. A good grade of top soil is placed in aluminum pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species are placed on the soil and pressed into the soil surface. The seeds and/or vegetative propagules are covered with soil and leveled. The pans are then placed on a sand bench in the greenhouse and watered from below as needed. After the plants reach the desired age (two to three weeks), each pan except for the control pans is removed individually to a spraying chamber and sprayed by means of an atomizer operating at a positive air pressure of approximately 1.46 kg/cm$^2$ absolute. The atomizer contains 6 ml. of a solution or suspension of the chemical. In that 6 ml., is an amount of a cyclohexanone emulsifying agent mixture to give a spray solution or suspension which contains about 0.4% by weight of the emulsifier. The spray solution or suspension contains a sufficient amount of the candidate chemical in order to give application rates corresponding to those set forth in the tables. The spray solution is prepared by taking an aliquot of a 1.0% by weight stock solution or suspension of the candidate chemical in an organic solvent such as acetone or tetrahydrofuran or in water. The emulsifying agent employed is a mixture comprising 35 weight percent butylamine dodecylbenzene sulfonate and 65 weight percent of a tall oil ethylene oxide condensate having about 11 moles of ethylene oxide per mole of tall oil. The pans are returned to the greenhouse and watered as before and the injury to the plants as compared to the control is observed at approximately two and four weeks as indicated in the tables under WAT and the results recorded. In some instances, the two-week observations are omitted.

The post-emergence herbicidal activity index used in Table I is as follows:

| Plant Response | Index |
|---|---|
| 0–24% control | 0 |
| 25–49% control | 1 |
| 50–74% control | 2 |
| 75–99% control | 3 |
| 100% control | 4 |

The plant species utilized in these tests are identified by letter in accordance with the following legend:

| | |
|---|---|
| A - Canada Thistle* | K - Barnyardgrass |
| B - Cocklebur | L - Soybean |
| C - Velvetleaf | M - Sugar Beet |
| D - Morningglory | N - Wheat |
| E - Lambsquarters | O - Rice |
| F - Smartweed | P - Sorghum |
| G - Yellow Nutsedge* | Q - Wild Buckwheat |
| H - Quackgrass* | R - Hemp Sesbania |
| I - Johnsongrass* | S - Panicum Spp |
| J - Downy Brome | T - Crabgrass |

*Established from vegetative propagules.

A dash (-) in the tables indicates that the particular species was absent in the test.

TABLE I

| Compound of Example No. | WAT | kg/h | A | B | C | D | E | F | G | H | I | J | K |
|---|---|---|---|---|---|---|---|---|---|---|---|---|---|
| I | 4 | 11.2 | 3 | 4 | 4 | 3 | 4 | 4 | 3 | 3 | 4 | 3 | 4 |
|  | 4 | 5.6 | 2 | 4 | 3 | 4 | 3 | 4 | 3 | 4 | 3 | 3 | 4 |
| II | 4 | 11.2 | 1 | 3 | 3 | 2 | 4 | 4 | 2 | 1 | 3 | 1 | 2 |
|  | 4 | 5.6 | 0 | 4 | 1 | 2 | 3 | 2 | 1 | 3 | 3 | 2 | 2 |
| III | 4 | 11.2 | 0 | 2 | 1 | 2 | 2 | 1 | 0 | 2 | 1 | 1 | 2 |
|  | 4 | 5.6 | 1 | 1 | 0 | 1 | 2 | 2 | 0 | 1 | 1 | 1 | 2 |
| IV | 4 | 11.2 | 1 | 3 | 1 | 2 | 3 | 2 | 1 | 1 | 0 | 1 | 2 |
|  | 4 | 5.6 | 0 | 1 | 0 | 2 | 3 | 1 | 0 | 2 | 2 | 0 | 2 |
| V | 4 | 11.2 | 1 | 3 | 0 | 2 | 3 | 2 | 1 | 4 | 2 | 1 | 3 |
|  | 4 | 5.6 | 0 | 2 | 1 | 1 | 3 | 1 | 1 | 1 | 1 | 1 | 3 |
| VI | 4 | 11.2 | 2 | 3 | 2 | 3 | 3 | 2 | 1 | 1 | 3 | 3 | 3 |
|  | 4 | 5.6 | 1 | 2 | 1 | 2 | 3 | 2 | 1 | 0 | 2 | 2 | 4 |
| VII | 4 | 11.2 | — | 2 | 1 | 1 | 2 | — | 1 | 1 | 2 | 2 | 3 |
|  | 4 | 5.6 | — | 1 | 1 | 1 | 2 | — | 2 | 1 | 3 | 2 | 3 |

TABLE II

| Compound of Example No. | WAT | kg/h | L | M | N | O | P | B | Q | D | R | E | F | C | J | S | K | T |
|---|---|---|---|---|---|---|---|---|---|---|---|---|---|---|---|---|---|---|
| I | 4 | 11.2 | 0 | 3 | 0 | 3 | 2 | 0 | 0 | 1 | 0 | 3 | 3 | 1 | 2 | 3 | 3 | 3 |
|  | 4 | 5.6 | 3 | 4 | 3 | 3 | 3 | 3 | 3 | 3 | 4 | 4 | 4 | 4 | 2 | 3 | 4 | 4 |
|  | 4 | 1.12 | 1 | 2 | 1 | 0 | 1 | 2 | 2 | 2 | 1 | 3 | 3 | 2 | 1 | 1 | 2 | 3 |
|  | 2 | 0.28 | 0 | 0 | 0 | 0 | 0 | 0 | 0 | 0 | 0 | 0 | 0 | 1 | 0 | 1 | 1 | 0 |
|  | 2 | 0.056 | 0 | 0 | 0 | 0 | 0 | 0 | 0 | 0 | 0 | 0 | 0 | 0 | 0 | 0 | 0 | 0 |
| II | 4 | 5.6 | 2 | 3 | 3 | 3 | 3 | 3 | 3 | 3 | 1 | 3 | 2 | 2 | 2 | 3 | 3 | 4 |
|  | 4 | 1.12 | 0 | 0 | 0 | 1 | 1 | 1 | 0 | 1 | 0 | 2 | 1 | 0 | 0 | 0 | 1 | 2 |
|  | 4 | 0.28 | 0 | 0 | 0 | 0 | 0 | 0 | 0 | 1 | 0 | 0 | 0 | 0 | 0 | 0 | 0 | 0 |
| IV | 4 | 5.6 | 2 | 4 | 3 | 1 | 2 | 3 | 2 | 2 | 1 | 3 | 2 | 2 | 3 | 3 | 4 | 4 |
|  | 4 | 1.12 | 0 | 3 | 1 | 0 | 0 | 1 | 0 | 0 | 0 | 3 | 1 | 0 | 0 | 0 | 0 | 2 |
|  | 2 | 0.28 | 0 | 0 | 0 | 0 | 0 | 0 | 0 | 0 | 0 | 0 | 0 | 0 | 0 | 0 | 0 | 0 |
| V | 4 | 5.6 | 1 | 2 | 3 | 1 | 0 | 3 | 0 | 1 | 1 | 3 | 2 | 1 | 0 | 1 | 3 | 3 |
|  | 4 | 1.12 | 0 | 2 | 1 | 0 | 0 | 1 | 0 | 1 | 2 | 3 | 3 | 0 | 0 | 0 | 0 | 2 |
|  | 2 | 0.28 | 0 | 0 | 0 | 0 | 0 | 0 | 0 | 0 | 0 | 0 | 0 | 0 | 0 | 0 | 0 | 0 |
| VI | 4 | 5.6 | 3 | 4 | 3 | 3 | 3 | 4 | 4 | 3 | 3 | 4 | 4 | 4 | 4 | 4 | 4 | 4 |
|  | 4 | 1.12 | 1 | 1 | 1 | 0 | 2 | 3 | 1 | 2 | 0 | 2 | — | 1 | 2 | 2 | 3 | 4 |

TABLE II-continued

| Compound of Example No. | WAT | kg/h | L | M | N | O | P | B | Q | D | R | E | F | C | J | S | K | T |
|---|---|---|---|---|---|---|---|---|---|---|---|---|---|---|---|---|---|---|
| | 4 | 0.28 | 0 | 0 | 0 | 0 | 0 | 0 | 0 | 0 | 0 | 0 | 0 | 0 | 0 | 0 | 0 | 0 |

EXAMPLE X

The pre-emergent herbicidal activity of various compounds of this invention is demonstrated as follows. A good grade of top soil is placed in aluminum pans and compacted to a depth of 0.95 to 1.27 cm. from the top of each pan. A predetermined number of seeds or vegetative propagules of each of several plant species are placed on top of the soil in each pan and then pressed down. Herbicidal compositions prepared as in the previous example are applied by admixture with or incorporation in the top layer of soil.

In this method, the soil required to cover the seeds and propagules is weighed and admixed with a herbicidal composition containing a known amount of the active ingredient (compound of this invention). The pans are then filled with the admixture and leveled. Watering is carried out by permitting the soil in the pans to absorb moisture through apertures in the pan bottoms. The seed and propagule containing pans are placed on a wet sand bench and maintained for approximately two weeks under ordinary conditions of sunlight and watering. At the end of this period, the number of emerged plants of each species is noted and compared to an untreated control. The data is given in Table III.

The pre-emergent herbicidal activity index used below is based upon average percent control of each species as follows:

| Percent Control | Index |
|---|---|
| 0–24% control | 0 |
| 25–49% control | 1 |
| 50–74% control | 2 |
| 75–100% control | 3 |

Plant species in the table are identified by the same code letters used in the previous example.

TABLE III

| Compound of Example No. | WAT | kg/h | A | B | C | D | E | F | G | H | I | J | K |
|---|---|---|---|---|---|---|---|---|---|---|---|---|---|
| I | 2 | 11.2 | 3 | 1 | 0 | 1 | 3 | 2 | 3 | 3 | 0 | 2 | 2 |
| II | 2 | 11.2 | 1 | 0 | 0 | 0 | 0 | 0 | 0 | 0 | 2 | 0 | 0 |
| III | 2 | 11.2 | 1 | 0 | 0 | 0 | 0 | 0 | 0 | 0 | 0 | 0 | 0 |
| IV | 2 | 11.2 | 3 | 0 | 0 | 0 | 0 | 0 | 0 | 1 | 0 | 0 | 0 |
| V | 2 | 11.2 | 2 | 0 | 0 | 1 | 0 | 1 | 0 | 1 | 3 | 2 | 3 |
| VI | 2 | 11.2 | — | 0 | 0 | 0 | 0 | — | 0 | 0 | 0 | 0 | 0 |

From the test results presented in Tables I and II, it can be seen that the post-emergent herbicidal activity of the compounds of this invention is, for the most part, general in nature. In certain specific instances, however, some selectivity is demonstrated. In this regard it should be recognized that each individual species selected for the above tests is a representative member of a recognized family of plant species.

From Table III, it can be seen that the pre-emergent herbicidal activity demonstrated some selectivity.

The herbicidal compositions, including concentrates which require dilution prior to application to the plants, of this invention contain from 5 to 95 parts by weight of at least one compound of this invention and from 5 to 96 parts by weight of an adjuvant in liquid or solid form, for example, from about 0.25 to 25 parts by weight of wetting agent, from about 0.25 to 25 parts by weight of a dispersant and from 4.5 to about 94.5 parts by weight of inert liquid extender, e.g., water, acetone, tetrahydrofuran, all parts being by weight of the total composition. Preferably, the compositions of this invention contain from 5 to 75 parts by weight of at least one compound of this invention, together with the adjuvants. Where required, from about 0.1 to 2.0 parts by weight of the inert liquid extender can be replaced by a corrosion inhibitor such as ethanol mercaptan, sodium thiosulfate, dodecylmono or dimercaptan or anti-foaming agent such as a dimethylpolysiloxane, or both. The compositions are prepared by admixing the active ingredient with an adjuvant including diluents, extenders, carriers and conditioning agents to provide compositions in the form of finely-divided particulate solids, pellets, solutions, dispersions or emulsions. Thus, the active ingredient can be used with an adjuvant such as a finely-divided solid, a liquid of organic origin, water, a wetting agent, a dispersing agent, an emulsifying agent or any suitable combination of these.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent", it is understood that wetting agents, dispersing agents, suspending agents and emulsifying agents are included therein. Anionic, cationic and non-ionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated orsulfonated fatty acid esters petroleum sulfonates, sulfonted vegetable oils, polyoxyethylene derivatives of phenols and alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin, sulfonates, polymeric alkyl naphthalene sulfonates, sodium naphthalene sulfonate, polymethylene bisnaphthalenesulfonate and sodium N-methyl-N-(long chain acid) taurates.

When operating in accordance with the present invention, effective amounts of the compounds or compositions of this invention are applied to the plants, or to soil containing the plants, or are incorporated into aquatic media in any convenient fashion. The application of liquid and particulate solid compositions to plants or soil can be carried out by conventional methods, e.g., powder dusters, boom and hand sprayers and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compounds or compositions of this invention to the plant is essential and critical for the practice of the present invention. The exact amount of active ingredient to be employed is dependent upon the response desired in the plant as well as such other factors as the plant species and stage of development thereof, and the amount of rainfall as well as the specific glycine employed. In foliar treatment for the control of vegetative growth, the active ingredients are applied in amounts from about 0.112 to about 56.0 or more kilograms per hectare. In pre-emergent treatments, the rate of application can be from about 5.6 to about 22.4 or more kilograms per hectare. In applications for the control of aquatic plants, the active ingredients are applied in amounts of from about 1.0 parts per million to about 1000 parts per million, based on the aquatic medium. An effective amount for phytotoxic or herbicidal control is that amount necessary for overall or selective control, i.e., a phytotoxic or herbicidal amount. It is believed that one skilled in the art can readily determine from the teachings of this specification, including examples, the approximate application rate.

There are several possible methods for applying liquid compositions of this invention to emerged plants. Such methods include the use of wiper systems whereby the plant to be treated is contacted with an absorbent material containing the particular liquid composition, a portion of which is thereby released onto the plant upon contact therewith. Such wiper systems typically comprise a reservoir of the liquid composition into which a portion of the absorbent material is placed and is fed therethrough. Generally, substances employable as absorbent material include substances of any shape or form capable of absorbing the liquid composition and releasing a portion of the same upon contact with the plant. Typical absorbent materials include felt, foam rubber, cellulose, nylon, sponges, hemp, cotton, burlap, polyester over acrylic, combinations thereof and the like. Forms of absorbent material include rope, twine, string, cloths, carpets, combinations thereof and the like. These forms may be assembled in any manner desired including a pipe rope wick, a wedge rope wick, a multi-rope wick and the like.

In another possible application method, liquid compositions may be selectively applied to weeds by the use of recirculating sprayer systems wherein the recirculating spray unit is mounted on a tractor or high clearance mobile equipment and the spray is directed horizontally onto the weeds growing over a crop. Spray not intercepted by the weeds is collected in a recovery chamber before contacting the crop and is reused. Roller applications may also be employed to apply liquid compositions to weeds growing over a crop.

In yet another possible application method, shielded applicators may be employed to direct the liquid composition in the form of a spray onto the weeds while effectively shielding the crops from the spray.

These and other possible application methods for selectively applying liquid compositions to weeds are discussed in detail in Innovative Methods of Post-Emergence Weed Control, McWhorter C. G., Southern Weed Science Society, 33rd Annual Meeting Proceedings, Jan. 15–17, 1980; Auburn University Printing Service, Auburn, Ala. U.S.A., the teachings of which are incorporated herein by reference in their entirety.

Another possible method of applying liquid compositions of this invention to plants includes controlled droplet application which is also known as the ultra low-volume chemical application. Controlled droplet application involves the production of uniform or nearly uniform spray drops of a predetermined size and the conveyance of these drops with negligible evaporation to a spray target. In particular, this method comprises feeding spray solutions to a rotary atomizer comprising a small disk with serrated edges that disperses liquid into droplets as the disk spins. Different droplet sizes are produced by changing solution flow rates to the spinning disk or changing the speed of rotation of the disk.

Those of skill in the art will recognize that the physical and chemical characteristics of the compound or composition employed will determine to a large extent the particular application method selected therewith.

The aforementioned and other methods for applying liquid compositions to plants are discussed in detail in "Rope Wick Applicator—Tool With A Future", Dale, James E., pp. 3–4, "The Recirculating Sprayer and Roundup ® Herbicide", Derting, Claude W., pp. 5–7, and "C.D.A. Herbicide Application", McGarvey, Frank X., *Weeds Today,* Volume 11, Number 2, pp. 8–9, Late Spring, 1980, 309 W. Clark St., Champaign, Ill., the teachings of which are incorporaed herein by reference in their entirety.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A process for preparing a compound of the formula

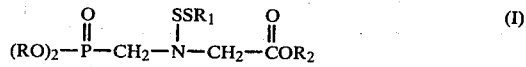

wherein R is selected from the group consisting of phenyl, naphthyl, biphenylyl; or phenyl, naphthyl or biphenylyl substituted with from 1 to 3 substituents, independently selected from the group consisting of lower alkyl, lower alkoxy, lower alkylthio, lower alkoxycarbonyl, methylenedioxy, trifluoromethyl, cyano, nitro and halogen; and $R_1$ is independently alkyl, cycloalkyl, aralower alkyl, phenyl, naphthyl or phenyl or naphthyl substituted with from 1 to 3 substituents independently selected from the group consisting of lower alkyl, lower alkoxy, halogen, trifluoromethyl and nitro, and $R_2$ is lower alkyl or aralower alkyl which comprises reacting a compound of the formula

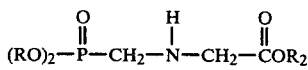

(II)

wherein R and R$_2$ are as aforedefined with SCl$_2$ aprotic solvent and in the presence of a hydrogen chloride acceptor to form a compound of the formula

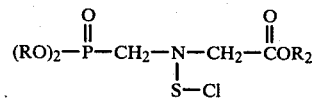

(III)

wherein R and R$_2$ are as above defined, and reacting said compound of formula (III) with a compound of the formula

(IV)

to form said compound of formula (I) and in the presence of a hydrogen chloride acceptor.

2. The process of claim 1, wherein R is phenyl.
3. The process of claim 2, wherein R$_1$ is alkyl.
4. The process of claim 3, wherein R$_1$ is methyl.
5. The process of claim 2, wherein R$_1$ is cycloalkyl.
6. The process of claim 5, wherein R$_1$ is cyclohexyl.
7. The process of claim 2, wherein R$_1$ is araloweralkyl.
8. The process of claim 7, wherein R$_1$ is phenylethyl.
9. The process of claim 3, wherein R$_1$ is isopropyl.
10. The process of claim 3, wherein R$_1$ is n-octyl.
11. The process of claim 3, wherein R$_1$ is tertiary alkyl.
12. The process of claim 11, wherein R$_1$ is tertiary butyl.
13. The process of claim 3, wherein R$_2$ is alkyl.
14. The process of claim 13, wherein R$_2$ is methyl.
15. The process of claim 3, wherein R$_2$ is aralower alkyl.
16. The process of claim 15, wherein R$_2$ is phenylmethyl.
17. The process of claim 2, wherein R$_1$ is phenyl or phenyl substituted with from 1 to 3 substituents independently selected from the group consisting of lower alkyl, lower alkoxy, halogen, trifluoromethyl and nitro.
18. The process of claim 1 wherein R is 4-chloro-3-methyl, phenyl R$_2$ is ethyl and R$_1$ is 4-methoxyphenyl.
19. The process of claim 2 wherein R is phenyl, R$_2$ is methyl and R$_1$ is 1,1-dimethylethyl.
20. The process of claim 2 wherein R is 4-methoxyphenyl, R$_2$ is ethyl and R$_1$ is 1,1-dimethylethyl.
21. The process of claim 2 wherein R is phenyl, R$_2$ is phenylmethyl and R$_1$ is 1,1-dimethylethyl.
22. The process of claim 2 wherein R is phenyl, R$_2$ is methyl and R$_1$ is 4-methylphenyl.
23. The process of claim 2 wherein R is 4-methoxyphenyl, R$_2$ is phenylmethyl and R$_1$ is naphthyl.
24. The process of claim 2 wherein R is 4-methoxyphenyl, R$_2$ is phenylmethyl and R$_1$ is 4-chlorophenyl.
25. The process of claim 2 wherein R is 4-chloro-3-methylphenyl.
26. The process of claim 2, wherein R$_1$ is isopropyl and R$_2$ is methyl.
27. The process of claim 2 wherein R$_2$ is ethyl.
28. The process of claim 2 wherein R$_1$ is 4-methoxyphenyl.
29. The process of claim 2, wherein said aprotic solvent comprises benzene, toluene, dichloromethane, tetrahydrofuran, dichloromethane, cyclohexane, methylcyclohexane, hexane, octane, dioxane, ethyl ether and mixtures thereof.
30. The process of claim 29, wherein said aprotic solvent comprises toluene.
31. The process of claim 30, wherein said hydrogen chloride acceptor is an amine.
32. The process of claim 31, wherein said amine is a tertiary amine.
33. The process of claim 32, wherein said tertiary amine is triethylamine.
34. The process of claim 33, wherein the temperature of said reaction is in the range from about −50° C. to about 100° C.
35. The process of claim 34, wherein said temperature is in the range from about −30° C. to about +10° C.
36. The process of claim 1, wherein the reaction of said compound of formula (II) with sulfur dichloride is carried out in the presence of an aprotic solvent.
37. The process of claim 1, wherein the reaction of said compound of formula (III) with said compound of formula (IV) is carried out in the presence of our aprotic solvent.

* * * * *